United States Patent
Gupta

(10) Patent No.: US 7,438,897 B2
(45) Date of Patent: Oct. 21, 2008

(54) TRANSPARENT COLD-WAX AND HOT-WAX DEPILATORY COMPOSITIONS WITH THREE-DIMENSIONAL SUSPENDED PARTICLES

(75) Inventor: Shyam K. Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 479 days.

(21) Appl. No.: 10/249,012

(22) Filed: Mar. 10, 2003

(65) Prior Publication Data

US 2004/0180014 A1  Sep. 16, 2004

(51) Int. Cl.
*A61K 8/00* (2006.01)
(52) U.S. Cl. ..................................... 424/70.1
(58) Field of Classification Search ................ 424/70.1, 424/400
See application file for complete search history.

(56) References Cited

U.S. PATENT DOCUMENTS

| | | | | |
|---|---|---|---|---|
| 4,282,877 A | * | 8/1981 | Mathews | 606/134 |
| 4,773,784 A | * | 9/1988 | Mann | 401/1 |
| 4,832,949 A | * | 5/1989 | Royal | 424/73 |
| 4,842,610 A | * | 6/1989 | Gordon et al. | 8/160 |
| 6,214,329 B1 | * | 4/2001 | Brieva et al. | 424/70.7 |
| 6,376,522 B1 | * | 4/2002 | Holzl et al. | 514/372 |
| 2002/0146380 A1 | * | 10/2002 | Nambu et al. | 424/70.16 |

FOREIGN PATENT DOCUMENTS

| | | | |
|---|---|---|---|
| EP | DE1986-240261 | * | 9/1986 |
| FR | 2 656 524 | * | 7/1991 |

\* cited by examiner

*Primary Examiner*—Michael G. Hartley
*Assistant Examiner*—Eric E. Silverman

(57) ABSTRACT

The present invention discloses cosmetic transparent hair removal (depilatory) compositions that: (1) Are transparent in appearance, (2) Can be made in cold wax or hot wax forms, (3) Manufactured at much less than 80 ° C., (4) Three-dimensional particles of visually attractive compositions can be added, (5) Bind more strongly with hair and less strongly with skin, (6) Can be applied either directly on the skin or applied on a piece of fabric, plastic, or paper first, which is then applied to skin for hair removal, and (7) Require minimal clean-up.

2 Claims, No Drawings

TRANSPARENT COLD-WAX AND HOT-WAX DEPILATORY COMPOSITIONS WITH THREE-DIMENSIONAL SUSPENDED PARTICLES

BACKGROUND OF INVENTION

Certain cold wax depilatory compositions (which are not transparent) have been disclosed by the present inventor in U.S. patent application Ser. No. 10/248,925 filed Mar. 3, 2003.

Various compositions and methods for removing hair (depilation) are known. For example, hair can be removed by electrolysis, by chemical action, or by physical removal. Various depilatory compositions, which utilize physical removal action, are described in, for example, U.S. Pat. Nos. 6,478,493; 5,847,363; 5,698,187; 5,848,850; 5,846,326; 5,158,765; 5,154,919; 5,840,765; 5,470,563; 5,154,919; 4,832,949; 2,091,313 and U.S. Patent Application 20030002912, among others.

Physical removal generally involves the use of wax or tacky tape. Generally, two types of wax for depilatory purposes are used for hair removal, a hot wax or a cold wax. Cold wax is gummy at room temperature, whereas hot wax is hard to medium hard at room temperature.

The hot wax compositions are typically heated above their melting point and coated onto the skin. Upon solidification, hair becomes trapped in the wax and is removed when the wax is peeled off the skin. During this process, some epidermal layers of skin are also removed or stripped away, exposing lower layers of skin and initiating inflammatory reaction from prostaglandin's formation. This is the principal reason for the development of skin irritation caused by the hot wax compositions. This fact has not been recognized by prior art. For example, prior art has focused mainly on the use of anti-irritants to circumvent this problem of skin irritation, as disclosed in U.S. Pat. No. 5,470,563 (Tanaka et al.).

In order to solve the problem of damage to skin from such heated depilatory compositions, several "cold-wax" hair removal compositions have been disclosed. Cold wax compositions do not require such a pre-heating or microwave step prior to their application for depilation. However, most such cold wax compositions are based on sugar or sugar derivatives. For example, U.S. Pat. No. 5,158,765 (Qasem) discloses a depilatory composition for the removal of hair that is composed of a mixture of sugar, water and aspirin. This mixture is heated to dissolve the solute materials, and then allowed to cool so as to form a soft, pliable composition that can be manually applied to the skin. The composition firmly adheres to the hair with which it comes in contact, and by quickly drawing the applied material away from the skin, will cause the hair to be removed from its roots. One problem from such compositions that are directly applied to skin is that usually an area larger than the area where depilation is needed is coated with such compositions, requiring a more extensive cleanup step after hair removal. Another problem is that such cold-wax compositions based on sugar or sugar derivatives do not remove all the hair in a single step, requiring two or more applications in the same area. This causes waste of product, additional skin irritation, and inconvenience.

Among other similar sugar-based compositions, U.S. Pat. No. 5,698,187 (Naggiar) discloses depilatory composition for the removal of hair from the human body that is composed of a mixture of maltodextrin, sucrose, water and citric acid. This mixture is heated to dissolve the solute materials, and then cooled to form a soft, pliant composition, which can be manually applied to the skin.

U.S. Pat. No. 4,842,610 (Gordon et al.) discloses hair removal compositions that comprise 90 to 99.5% corn syrup and 0.5% to 10% added water by weight. The compositions are used by applying them to the surface of the skin in a hairy area, pressing a sheet of paper or other fibrous material against the area and subsequently lifting the sheet of fibrous material or peeling it off the skin surface.

U.S. Pat. No. 4,832,949 (Royal) discloses a depilatory composition for removal of hair from the human skin that is made up of a mixture of honey, sugar and citric acid which mixture is heated to a predetermined temperature level, then allowed to cool so as to form a highly viscous, wax-like composition which can be applied manually in slender strips to the skin.

It is commonly recognized that sugar-based compositions do not remove hair adequately in a single application, as mentioned above. The most preferred depilatory compositions are based on rosin or rosin derivatives, or polymers. However, such compositions must be applied in hot state, causing the problems of inconvenience, burns, skin irritation, extensive cleanup after use, and such as mentioned earlier. Sugar and sugar derivatives based compositions, on the other hand, contain substantial amounts of water, or alcohol, or mixtures of water and alcohol, which tend to evaporate each time a bottle is opened for product application, thus resulting in the crystallization of sugar or sugar derivatives from such compositions. Such crystallizations cause a loss of the hair removing power of such compositions, and also make it harder for the bottle to be opened for product use. U.S. Pat. No. 6,417,346 (Salome et al.) further discusses such sugar solution crystallization problems. Additionally, a "dry-down" period is required for such sugar and sugar derivatives based compositions after product applications to let water or alcohol partially evaporate, and before the depilation step is completed. This "dry-down" period can be from 5 minutes to 20 minutes, or even longer. The product does not gain sufficient "stickiness" to remove hair if this "dry-down" period is not observed.

Most hot wax compositions are opaque and not elegant in appearance or application on skin. For example, they cannot be made in different colors, or contain mica and other visually appealing compositions to give a shiny, brilliant appearance with particles suspended and visible in a three-dimensional manner.

Some cold wax compositions can be made in transparent form. However, they are mostly made from sugar and sugar derivatives that lack hair removal efficacy in a single application. Also, the rheological properties of such compositions do not permit the inclusion of visibly attractive particles or additives that can remain suspended in a three-dimensional manner in a stable composition. Most sugar and sugar derivatives based transparent compositions are greatly sensitive to storage temperature conditions that frequently result in the re-agglomeration of any suspended particles included in such compositions for visual aesthetics.

Also, as mentioned earlier, the skin irritation is caused mostly by the stripping of the upper layers of skin from such sticky depilatory compositions of both hot wax and cold wax forms. It would be ideal if such compositions can adhere preferentially to hair, and not skin. Although not bound by any theory, it should be possible to achieve this in such a selective manner.

It is well known that hair possesses more hydrophobic properties than skin. Hair is more tightly composed due to the presence of sulfur amino acids (cysteine and cystine) in its keratin structure. Skin, on the other hand, is known to contain a large amount of hydrophilic amino acids. If a depilatory composition can be devised to bond more strongly with hydrophobic groups of hair and cause less strong bonding with skin surface taking advantage of skin's more hydrophilic surface, then such a bonding would provide more selective adherence to hair surface, thus causing hair removal much easier, and causing much less disruption of the upper layers of skin.

In addition, most current manufacturing procedures for both cold wax and hot wax compositions require heating of a mixture of solid and liquid components at the dissolution temperatures of the solid components in the liquid components. Such temperatures usually exceed 100° C. for prolonged period of time till such dissolutions are complete. These compositions must be constantly mixed during this time. It is also frequent that the total solid components in such compositions are more predominant, usually in excess of 80%. This makes the mixing process very difficult for such compositions. Additionally, such high temperatures and prolonged periods of heating during the manufacturing process cause significant degradation, oxidation, and discoloration of components. It is also difficult to add perfumes, colorants, and many visually attractive ingredients in such compositions due to such high temperature requirements.

It would thus be advantageous to devise manufacturing processes for both cold wax and hot wax compositions that require much lower temperatures for processing, for example, not exceeding 80° C., and also contain a greater amount of liquid components to improve mixing process. It would be preferred to have at least 30% of total liquid components in such compositions for industrially convenient manufacturing process.

It would thus be advantageous if a depilatory composition can be made that has the following properties: (1) It is transparent in appearance, and (2) It can be made in either cold wax or hot wax forms, and (3) It is manufactured at much less than 100° C., and (4) Three-dimensional colored or shiny particles made of plastic, mica, metal, ceramic, cloisonn é, and other visually attractive compositions can be added that remain stable under the conditions of storage and use, and (5) It can bind more strongly with hair and less strongly with skin, and (6) It can be applied either directly on the skin or applied on a piece of fabric, plastic, or paper first, which is then applied to skin for hair removal, and (7) Require minimal clean-up, and (8) Additional skin and hair beneficial ingredients, such as hair growth retardants, anti-irritants, topical pain relief agents, antioxidants, skin soothing agents, skin cooling agents, emollients, moisturizers, topical anesthetics, colorants, botanical extracts, fragrances, and such can be included.

SUMMARY OF INVENTION

The present invention discloses cosmetic hair removal (depilatory) compositions suitable for site-specific face or body applications that provide the following benefits (1) Transparent in appearance, and (2) Can be made in either cold wax or hot wax forms, and (3) It is manufactured at much less than 100° C., and (4) Three-dimensional colored or shiny particles made of plastic, mica, metal, ceramic, cloisonn é, and other visually attractive compositions can be added that remain stable under the conditions of storage and use, and (5) Bind more strongly with hair and less strongly with skin, and (6) Can be applied either directly on the skin or applied on a piece of fabric, plastic, or paper first, which is then applied to skin for hair removal, and (7) Require minimal clean-up, and (8) Additional skin and hair beneficial ingredients, such as hair growth retardants, anti-irritants, topical pain relief agents, antioxidants, skin soothing agents, skin cooling agents, emollients, moisturizers, topical anesthetics, colorants, botanical extracts, fragrances, and such can be included.

Based on the above properties required for transparent depilatory compositions, the present invention discloses such compositions that are based on: (1) A hair binding agent or composition, and (2) A solubilizing transparency enhancing composition, and optionally (3) A rheology modifier, and, optionally (4) Three-dimensional suspended visual aesthetic enhancing compositions, and, optionally (5) An emollient, skin slip agent, or skin protectant agent, or composition.

DETAILED DESCRIPTION

Cosmetic hair removal (depilatory) compositions suitable for site-specific face or body applications that provide the following benefits (1) Transparent in appearance, and (2) Can be made in cold wax or hot wax forms, and (3) It is manufactured at much less than 100° C. with better mixing, and (4) Three-dimensional colored or shiny particles made of plastic, mica, metal, ceramic, cloisonn é, and other visually attractive compositions can be added that remain stable under the conditions of storage and use, and (5) Bind more strongly with hair and less strongly with skin, and (6) Can be applied either directly on the skin or applied on a piece of fabric, plastic, or paper first, which is then applied to skin for hair removal, and (7) Require minimal clean-up, and (8) Additional skin and hair beneficial ingredients, such as hair growth retardants, anti-irritants, topical pain relief agents, antioxidants, skin soothing agents, skin cooling agents, emollients, moisturizers, topical anesthetics, colorants, botanical extracts, fragrances, and such can be included.

Based on the above properties required for a transparent cold wax and hot wax depilatory compositions, the present invention discloses such compositions that are based on: (1) A hair binding agent or composition, and (2) A solubilizing transparency enhancing composition, and, optionally (3) A rheology modifier, and, optionally (4) Three-dimensional suspended visual aesthetic enhancing compositions, and, optionally (5) An emollient, skin slip agent, or skin protectant agent, or composition.

It is well known that hair is more hydrophobic and less hydrophilic than skin and it contains a much larger amount of sulfur-containing amino acids, cysteine and cystine in its keratin protein structure. Skin, on the other hand, is known to contain a large amount of acidic amino acids that gives skin surface both an acidic pH and more hydrophilic nature. Such differential physical and chemical properties of hair and skin have not been utilized in the prior art depilatory compositions for selective removal of hair without damage to skin by undesirable excessive exfoliation from such compositions that can cause skin irritation and infection.

Surprisingly and unexpectedly, it has now been discovered that hair can be bound selectively, while skin is provided with a lubricating film for slip and protective emolliency that does not reduce the binding of hair with depilatory compositions of the present invention. Yet, the same ingredients or compositions that provide a lubricating or protective film on the skin for slip also induce transparency in the compositions of the present invention.

The hair bonding agent or compositions can be selected from a wide number of rosin, rosinates, and polymers that can be utilized either alone or in combination. The examples include, but not limited to Wood Rosin, Rosin Esters, Modified Rosin Esters, Glyceryl Rosinate, Glyceryl Hydrogenated Rosinate, Polyethylene Glycol Rosinate, Polyethylene Glycol Hydrogenated Rosinate, Pentaerythritol Rosinate, Pentaerythritol Hydrogenated Rosinate, Polyvinyl Alcohol, Polyvinyl Acetate, Polyvinyl Esters, PVP, PVP/PVA Copolymers, Dimerized Rosin, Esters of Dimerized Rosin, Modified Wood Rosin, Esters of Modified Wood Rosin, Polyol Ester Rosinate, Polyterpene Resins, Esters of Hydrogenated Modified Rosin; (Hydrogenated Rosins covers both fully and partially hydrogenated forms), Polyethylene, Polypropylene, Polystyrene, Polyisobutylenes, EVA Resins, Block Copolymers, Polyvinyl Ethers, Polyacrylics, Polyvinyl butyral, Polyamides, Aromatic Hydrocarbon Resin, Cellulose Acetate, Ethyl Cellulose, Cellulose Acetate Butyrate, Ethyl Hydroxyethylcellulose, Nitrocellulose, Alkyl Resins, Rosin Ester Resins, Hydrocarbon waxes, Natural Waxes, Shellac, Natural Rubber, Styrene-Butadiene Rubber, Nitrile Rubber, Butyl Rubber, Polychloroprene Rubber, and Chlorinated Rubber.

The compositions of the present invention also include at least one solubilizing transparency enhancing composition. The purpose of this additive is to solubilize any crystal forming or crystallizing components of the composition to enhance and stabilize the transparent appearance of the composition over extended periods of storage or repeated use. The solubilizing transparency enhancing composition generally have a meting or softening point preferably less than 80° C., more preferably less than 50° C., and most preferably less than 40° C., and can be selected from including, but not limited to, resins (such as rosinates, rosinate esters, rosinate derivatives); long carbon-chain alcohol or fatty alcohols and their alcohol ethoxylates and propoxylates (such as polyethylene glycol, polypropylene glycol, polybutylene glycol, carbowax derivatives, Laureth-3, Laureth-4, Polysorbates, Polysorbate Esters, Polyglyceryl Stearates, propylene glycol, methylpropanediol, butylene glycol, hexylene glycol, ethoxydiglycol); certain silicone derivatives (such as dimethicone, Dimethiconol, dimethicone Polyol, alkyl dimethicones, alkyl dimethicone copolyols); certain amino and amido alcohols (such as Cocamid DEA, Cocamid MEA, and such); certain natural oils and butters (such as almond oil, castor oil, linseed oil, sunflower seed oil, mango oil, coconut oil, corn oil, vegetable oil, sesame seed oil, jojoba oil, pistachio nut oil, macadamia nut oil, mango butter, coco butter, almond butter, shea butter, aloe butter, sal butter, kokum butter, butters made from hydrogenated natural oils, and such); and combinations thereof. When one rosin derivative is used as a hair binding agent and another such derivative is used as solubilizing transparency enhancing composition, then the melting or softening point of the latter is most preferably at least 10° C. lower than the melting or softening point of the former such derivative.

It is not clear as to how the above solubilizing transparency enhancing compositions actually work. It is a hypothesis of the present inventor (and not a proven fact) that the hair binding compositions that are either carboxylic acid or ester derivatives of various resins, when heated in the presence of a hydroxylic transparency enhancing composition, react either fully or partially with such hydroxylic compositions to give corresponding substituted resins (by esterification or ester-interchange reactions) that induce transparency in such compositions (Equation 1).

Rosin-CO—O—R+R$^1$—OH=Rosin-CO—O—R$^1$+ R—OH  (Equation 1)

Moreover, and quite surprisingly, such chemical transformations also result in better binding with hair and less binding with skin surface of such depilatory compositions. Hair binding compositions that are either carboxylic acid or ester derivatives of various resins, when heated in the presence of a Silicone Polyol or Alkyl Silicone Polyol transparency enhancing composition, react either fully or partially with such silicone polyol compositions to give corresponding silicone substituted resins (in a chemical manner similar to Equation 1) that induce transparency.

In the cases where a higher melting point rosinate is mixed with a lower melting point rosinate for the preparation of a hot-wax transparent depilatory composition of the present invention, the mechanism of translucency enhancement, although not known at this time, may simply be caused by the realignment of the molecules of higher melting rosinate by the molecules of the lower melting point rosinate. The cause for the transparency enhancement by natural oils and butters, when used in combination with a higher melting point rosinate, may also be similar. Although the cause for the transparency enhancement by natural oils and butters is not definitely known at this time, it is also hypothesized that such natural oils and butters, being glycerides of fatty acids, may also undergo trans-esterification reaction with rosinates-type hair binding compositions to form in-situ corresponding fatty acid esters of rosinates, the latter are possibly also responsible for the translucency enhancement due to their inhibition of the crystallization of rosinates in such transparent depilatory compositions. Thus, whether the mechanism involves a trans-esterification reaction, or a molecular realignment as discussed above, or both, is not well known at this time. Surprisingly, again, such mechanisms also cause greater binding with hair and less strong binding with skin surface. It is even more surprising that only a small amount of such trans-esterification or molecularly realigned rosinates can still cause such an improvement in the benefits provided by the compositions of the present invention.

The hot-wax compositions can be made also from cold-wax compositions of the present invention by also including a rheology modifier component. The function of the rheology modifier is to increase the viscosity of the cold-wax composition (which is usually formulated in a liquid or thick liquid form) to increase the hardness (when cooled to ambient temperature), and thus formed hot-wax composition is clear and transparent. Such hot-wax compositions require a pre-heating or microwave step at a much lower temperature than prior art compositions before their application on skin for hair removal. Also, hot-wax compositions of the present invention remain in a liquid state at much lower temperatures also, for example at 40° C. or less. This causes greater thermal stability of such compositions and much safer use without causing any burns or damage to skin. In practice, by the inclusion of a rheology modifier to a cold-wax composition it is possible to convert a cold-wax composition into a hot-wax composition. This offers much convenience in manufacturing and reduction of product costs. The three-dimensional visual additives can also be included in such hot-wax compositions. However, it is surprising that such three-dimensional visual additives or compositions that are added still remain suspended uniformly in hot-wax depilatory compositions of the present invention, despite their repeated heating and cooling cycles during their application for depilation.

The three-dimensional visual aesthetics enhancing compositions can be optionally selected from a great number of materials available that includes colored or coated Microcapsules, Shimmer (such as mica, mica derivatives), Beads (such as Polyethylene), Polyethylene Glitter, Sand, Nut Shells, Botanical Fragments (leaf, flower, herb, sea weed), and their combinations. It is to be appreciated by those versed in the art that the size of such three-dimensional visual enhancement additives should not be too large to interfere with the bonding of depilatory compositions with hair for efficient depilation.

The inclusion of a protective skin coating composition in the compositions of the present invention is optional. As has become evident above, certain transparency enhancing compositions also function, quite surprisingly, also as skin coating agents since they cause stronger binding with hair and less strong binding with skin surface. Therefore, the use of a protective skin composition is optional. The purpose of such compositions is to provide slip during the pulling of the fabric, plastic, or paper for hair removal, thus protecting any damage to the upper layers of skin during depilation process. This makes the removal of the composition from the skin surface easier, thus eliminating or significantly reducing any damage to the outer layers of skin that can cause the skin irritation or infection, as commonly experienced with other rosin, Rosinate, or polymer based depilatory compositions.

The protective skin coating agent can be selected from, but not limited to, natural oils, natural butters, natural waxes, synthetic oils, synthetic waxes, silicone oils, silicone waxes, silicone elastomers, Silicone Rosinates, Alkoxylated Silicone Rosinates, organic siloxanes, and their cross polymer (e.g., dimethicone, dimethicone copolyol, cetyl dimethicone copolymer, cetyl dimethicone, stearyl dimethicone, stearoxydimethicone, behenoxydimethicone, alkyl methicone, amodimethicone, dimethicone alkyl betaine, cyclomethicone, polydimethylsiloxane, diphenyldimethyl polysiloxane, silicone elastomers, cyclomethicone and dimethicone crosspolymer, Jeesilc 6056, Dow Corning 2501, modified celluloses, hydroxyethyl cellulose, ethyl cellulose, carboxymethyl cellulose, ethyl hydroxyethyl cellulose, xanthan gum, gellan gum, guar gum, cationic polymers, Aristoflex AVC (Ammonium Acryloyldimethyltaurate/VP Copolymer), Structure Plus and Structure XL (Acrylates/Aminoacrylates/c10-30 Alkyl PEG-20 Itaconate Copolymer), Carbomer, Carbopol ETD 2020 (Acrylate C10-30 Alkyl Acrylate Crosspolymer), Rheocin (trihydroxystearin), Hydramol PGDS (PEG-90 Diisostearate), C24-28 Alkyl Dimethicone, Behenyl alcohol, quaternary ammonium compounds, sugar, sugar derivatives, corn syrup, honey, maltodextrin, and combinations thereof.

A number of hair growth retardants are also known. It is commonly known that such hair growth retardants usually provide better action if applied to skin immediately after depilation process. The optional inclusion of such hair growth retardants in the depilatory compositions should provide additional advantages in that the depilatory step would be required less frequently. The inclusion of such hair growth retardants is not possible in the compositions that require a high temperature manufacturing step, as most hair growth retardants are not stable under the conditions of heating. Since the compositions of the present invention do not require a high temperature heating step, such hair growth retardants can now be included. Examples of such hair growth retardant compositions that can be included are, but not limited to, U.S. Pat. No. 5,908,867 (Henry et al.), U.S. Patent Applications 20030036561 (Stykzynski et al.), 20030026776 (Shibuta et al.), 20020197290 (Di Pierro), 20020146404 (Tsuji et al.), U.S. Pat. Nos. 6,414,017; 6,239,170; 6,248,751 (Ahluwalia et al.), U.S. Pat. No. 6,407,056 (Sieberg et al.), U.S. Pat. No. 6,375,948 (Tsuji et al.), U.S. Pat. Nos. 6,299,865; 6,235,737 (Styczynski et al.), and U.S. Pat. Nos. 6,218,435; 6,121,269 (Henry et al.) among others, and various commercially marketed compositions, such as Pilinhibit, Capislow (Sederma/Croda).

Additional skin and hair beneficial ingredients or compositions can also be included optionally in the compositions of the present invention. Since a high temperature manufacturing step is not necessary for compositions of the present invention, such additives remain stable and chemically unaltered in such compositions. The examples include, but not limited to, skin soothing agents, antioxidants, topical anesthetics, antibacterial agents, emollients, moisturizers, skin surface cleansing agents, botanical extracts, perfumes, colorants, preservatives, color stabilizers, antioxidants for rancidity control and such, and combinations thereof can also be included in amounts that are safe and sufficient for their intended benefits and functions.

Although the compositions of the present invention do not cause irritation or pain during depilation process, it may be desirable to optionally include skin cooling and skin numbing agents for some consumers who have delicate, sensitive skin. The examples of such ingredients that can be selected for this purpose includes, but not limited to, menthol, menthol esters, methyl salicylate, camphor, benzocaine, dibucaine, dyclonine, lidocaine, pramoxine, tetracaine, ephedrine, epinephrine, phenylephrine, and their derivatives, and combinations thereof.

It is worthy of note that the compositions of the present invention can be made at temperatures much less than 80° C., as further illustrated in the Examples section of the present invention. This is of special significance since all previously known hot-wax compositions based on rosinates and cold-wax compositions based on sugar and sugar derivatives have all required processing temperatures much above 80° C., usually 100° C., or even higher. The compositions of the present invention provide far more convenient commercial manufacturing process, and a much greater number of other additives, fragrances, and compositions can also be included, since they can now be added at temperatures in the range of 40 to 45° C. after mixing of the main batch is complete and batch has been cooled down to a lower temperature for the addition of any temperature sensitive ingredients or compositions.

EXAMPLES

The following examples are presented to illustrate presently preferred practice thereof. As illustrations they are not intended to limit the scope of the invention. All quantities are in weight %

Example 1

Transparent Cold-Wax Depilatory Composition. Ingredient % (1) Modified Rosin Ester (melting point 25° C.) 95.0 (2) Polypropylene Glycol 4.8 (3) Tetradibutyl pentaerythrityl Hydroxyhydrocinnamate (a color stabilizer) 0.2 Procedure. Mix all components and heat at 60 to 65° C. to a clear liquid. Cool to room temperature. A clear, transparent light yellow gel-like liquid is obtained. It is applied to skin or pre-cut fabric, plastic, or paper without any pre-heating or microwave.

Example 2

Transparent Cold-Wax Depilatory Composition with Three-Dimensional Suspended Mica. Ingredient % (1) Rosin Ester (melting point 30° C.) 95.0 (2) Polypropylene Glycol 4.0 (3) Golden Mica Glitter 0.8 (4) Tetradibutyl pentaerythrityl Hydroxyhydrocinnamate 0.2 Procedure. Mix all components and heat at 60 to 65° C. to a clear liquid. Cool to room temperature. A clear, transparent light yellow gel like liquid is obtained that contains suspended golden mica particles.

Example 3

Transparent Hot-Wax Depilatory Composition. Ingredient % (1) Glyceryl Hydrogenated Rosinate (melting point 80° C.) 25.8 (2) Modified Rosin Ester (melting point 25° C.) 70.0 (3) Mango butter (and) shea butter (and) sal butter (and) grape seed oil (and) kiwi seed oil 4.0 (4) Tetradibutyl pentaerythrityl Hydroxyhydrocinnamate 0.2 Procedure. Mix all components and heat at 70 to 75° C. to a clear liquid. Cool to room temperature. A transparent, light amber non-mobile gel is obtained.

Example 4

Transparent Hot-Wax Depilatory Composition with Three-dimensional Suspended Polyethylene Particles. Ingredient % (1) Glyceryl Hydrogenated Rosinate (melting point 80° C.) 28.8 (2) Modified Rosin Ester (melting point 25° C.) 70.0 (3) Colored Polyethylene particles 1.0 (4) Tetradibutyl pentaerythrityl Hydroxyhydrocinnamate 0.2 Procedure. Mix all components and heat at 65 to 70° C. to a clear liquid. Cool to room temperature. A clear, transparent gel with suspended colored polyethylene particles is obtained.

Example 5

Preparation of a Transparent Hot-Wax Composition from a Transparent Cold-Wax Composition. Ingredient % (1) Transparent Cold-Wax Composition (from Example 1) 70.0 (2) Glyceryl Hydrogenated Rosinate (melting point 80° C.) 30.0 Procedure. Heat (1) at 70 to 75° C. till a clear solution is obtained. Add (2) and mix till a clear solution is obtained. Cool to room temperature. A clear transparent non-mobile gel like product is obtained.

Example 6

Transparent Cold-Wax Depilatory Composition with a Hair Growth Retardant and Fragrance. Ingredient % (1) Modified Rosin Ester (melting point 25° C.) 94.0 (2) Castor Oil 3.8 (3) Tetradibutyl pentaerythrityl Hydroxyhydrocinnamate (a color stabilizer) 0.2 (4) Pilinhibit 1.0 (5) Fragrance 1.0 Procedure. Mix (1) to (3) and heat at 60 to 65° C. to a clear liquid. Cool to 40 to 45° C. and add (4) and (5) and mix. Cool to room temperature. A clear, transparent light yellow gel-like composition is obtained. It is applied to skin or pre-cut fabric, plastic, or paper without any pre-heating or microwave.

I claim:

1. A method for removing hair from a human body, which comprises:
   (1) providing a cold wax transparent depilatory composition, said cold wax transparent depilatory composition comprising
      (i) a polypropylene glycol as a solubilizing transparency enhancing agent, wherein the polypropylene glycol is present from 1 to 50 weight percent, and
      (ii) a hydrophobic rosin selected from the group consisting of wood rosin, rosin esters, modified rosin esters, glyceryl rosinate, glyceryl hydrogenated rosinate, polyethylene glycol rosinate, polyethylene glycol hydrogenated rosinate, pentaerthritol rosinate, pentaerythritol hydrogenated rosinate, dimerized rosin, esters of dimerized rosin, modified wood rosin, esters of modified wood rosin, polyol ester rosinate, polyterpene rosins, esters of hydrogenated modified rosin, aromatic hydrocarbon rosin, rosin ester resins, and combinations thereof, wherein the hydrophobic rosin is present in 50 to 99 weight percent
   (2) mixing and heating said cold wax transparent depilatory composition to at least its melting or softening point, wherein the heating is to a temperature not exceeding 80 degrees Celsius
   (3) cooling said cold wax transparent depilatory composition to a temperature of 30 degrees Celsius or less
   (4) applying said cooled cold wax transparent depilatory composition to the skin containing the hair to be removed, and
   (5) peeling said cold wax depilatory composition from the skin, thereby removing hair caught in said cold wax depilatory composition.

2. The method of claim 1, wherein said hydrophobic rosin is Modified Rosin Ester.

* * * * *